(12) United States Patent
Decre et al.

(10) Patent No.: US 9,144,681 B2
(45) Date of Patent: *Sep. 29, 2015

(54) DEVICE FOR MODULATION OF NEURAL SIGNALS

(71) Applicant: Sapiens Steering Brain Stimulation B.V., Eindhoven (NL)

(72) Inventors: Michel Marcel Jose Decre, Eindhoven (NL); Hubert Cecile Francois Martens, Eindhoven (NL); Youri Victorovitch Ponomarev, Eindhoven (NL)

(73) Assignee: Medtronic Bakken Research Center B.V., Maastricht (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/548,776

(22) Filed: Nov. 20, 2014

(65) Prior Publication Data

US 2015/0080987 A1    Mar. 19, 2015

Related U.S. Application Data

(63) Continuation of application No. 12/519,813, filed as application No. PCT/IB2007/055215 on Dec. 18, 2007, now Pat. No. 8,923,977.

(60) Provisional application No. 60/871,227, filed on Dec. 21, 2006.

(51) Int. Cl.
*A61N 1/08* (2006.01)
*A61N 1/36* (2006.01)
(Continued)

(52) U.S. Cl.
CPC .......... *A61N 1/36139* (2013.01); *A61N 1/0526* (2013.01); *A61N 1/0529* (2013.01);
(Continued)

(58) Field of Classification Search
CPC ............ A61N 1/36067; A61N 1/0529; A61N 1/0526; A61N 1/0534; A61N 1/3605; A61N 1/36025; A61N 1/36139
USPC .................................. 607/2, 48, 62, 116, 118
See application file for complete search history.

(56) References Cited

U.S. PATENT DOCUMENTS

| 5,913,882 A | 6/1999 | King |
| 8,923,977 B2 * | 12/2014 | Decre et al. ..................... 607/48 |
| 2005/0113744 A1 * | 5/2005 | Donoghue et al. .............. 604/66 |

FOREIGN PATENT DOCUMENTS

| EP | 0959942 A1 | 6/2003 |
| EP | 1191972 1 | 8/2005 |

(Continued)

OTHER PUBLICATIONS

Song et al: "Physiologically Plausible Stochastic Nonlinear Kernel Models of Spike Train to Spike Train Transformation"; Proceedings of the 28th IEEE Annual International Conference of the Engineering in Medicine and Biology Society (EMBS), August 2006, vol. 1, pp. 6129-6132.
Berger et al: "Brain-Implantable Biomimetic Electronics as the Next Era in Neural Prosthetics"; Proceedings of the IEEE, vol. 89, vol. 7, Jul. 2001, pp. 993-1012.

(Continued)

*Primary Examiner* — Christopher D Koharski
*Assistant Examiner* — Michael Carey
(74) *Attorney, Agent, or Firm* — Shumaker & Sieffert, P.A.

(57) ABSTRACT

A neuromimetic device includes a feedforward pathway and a feedback pathway. The device operates in parallel with a suspect neural region, coupled between regions afferent and efferent to the suspect region. The device can be trained to mimic the suspect region while the region is still considered functional; and then replace the region once the region is considered dysfunctional. The device may be particularly useful in treating neuromotor issues such as Parkinson's disease.

26 Claims, 7 Drawing Sheets

(51) Int. Cl.
*A61N 1/05* (2006.01)
*A61N 2/00* (2006.01)

(52) U.S. Cl.
CPC ............ *A61N1/0534* (2013.01); *A61N 1/3605* (2013.01); *A61N 1/36025* (2013.01); *A61N 1/36067* (2013.01); *A61N 1/36021* (2013.01); *A61N 1/36082* (2013.01); *A61N 2/006* (2013.01)

(56) References Cited

FOREIGN PATENT DOCUMENTS

| RU | 2081637 | C1 | 6/1997 |
|---|---|---|---|
| RU | 2214842 | C1 | 10/2003 |
| WO | 2005053787 | A1 | 6/2005 |

OTHER PUBLICATIONS

Berger et al:"Brain-Implantable Biomimetic Electronics as Neural Prosthetics"; Proceedings of the 25th Annual International Conference of the the IEEE Engineering in Medicine and Biology Society (EMBS), Sep. 2003, vol. 2 pp. 1956-1959.

Berger et al: "Implantable Biomimetic Electronics as Neural Prostheses for Lost Cognitive Function"; Proceedings of the 2005 IEEE International Joint Conference on Neural Networks; IEEE, vol. 5, Jul. 2005, pp. 3109-3114.

Zumsteg et al: "Power Feasibility of Implantable Digital Spike Sorting Circuits for Neural Prosthetic Systems"; IEEE Transactions on Neural Systems and Rehabilitiona Engineering, vol. 13, No. 3, Sep. 2005, pp. 272-279.

Temel et al: "The Functional Role of the Subthalamic Nucleus in Cognitive and Limbic Circuits"; Progress in Neurology, vol. 76 (2005), pp. 393-413.

Prosecution History from U.S. Appl. No. 12/519,813, dated from Nov. 26, 2012 through Aug. 22, 2014, 32 pp.

* cited by examiner dt = DELAY BETWEEN 1 AND 2
δ = MODULATION OF OUTPUT PARAMETER
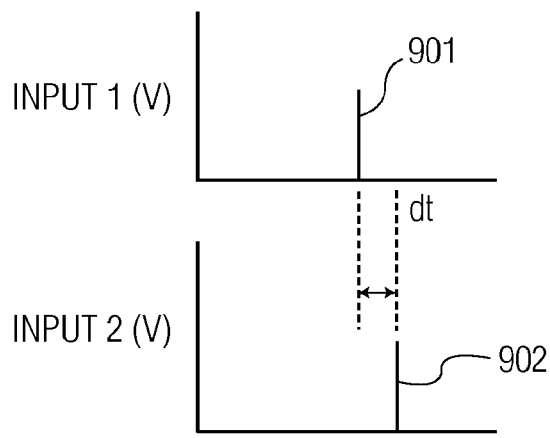
FIG. 9A
FIG. 9B
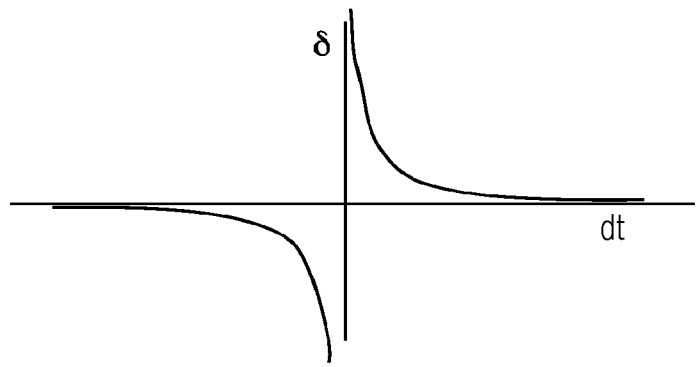
FIG. 9C
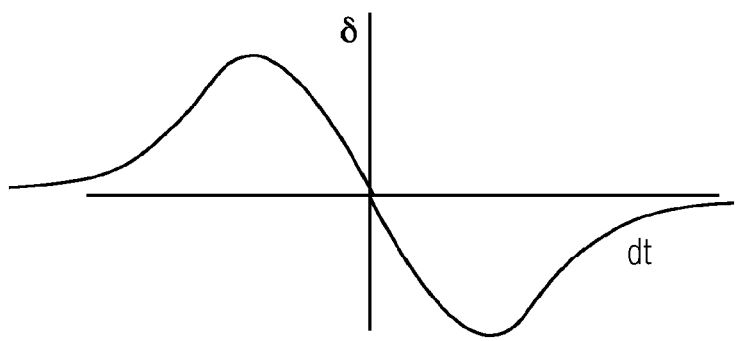
FIG. 9D

DEVICE FOR MODULATION OF NEURAL SIGNALS

CROSS-REFERENCE TO RELATED APPLICATIONS

This application is a continuation of U.S. patent application Ser. No. 12/519,813 filed on Dec. 18, 2007 which is a U.S. National Stage of International Patent Application No. PCT/IB2007/055215 filed on Dec. 18, 2007, which claims priority to U.S. Provisional Patent Application No. 60/871,227 filed on Dec. 21, 2006, all of which are incorporated herein by reference in their entirety.

The present application relates to the field of biomimetic neurostimulation devices.

An alternative treatment for neurological disorders is neurostimulation therapy. Such therapy applies electric or magnetic stimuli to neural tissues by means of external or implanted devices. A biomimetic neurostimulation device is described in Berger et al., "Brain Implantable Biomimetic Electronics as the next Era in Neural Prosthetics," Proc. IEEE, Vol. 89, #7, July 2001 pp. 993-1012. This document describes an electronic model of the input-output transformation by the hippocampus.

It is desirable to make the known device more adaptable and flexible.

Objects and advantages will be apparent from reading the specification and claims that follow. It will be apparent from the following specification that a more adaptable and flexible device can be used as a prosthetic for compromised tissue and include at least one signal processing apparatus that includes a feed-forward path and a modulation path. The feed-forward path simulates neurological signal processing between regions afferent and efferent to a suspect region. The modulation path informs the feed-forward path responsive to signals received elsewhere. The modulation path can feed back signals even further efferent than an output of the feed-forward path.

Disorders potentially treatable with this therapy include motor disorders, cognitive disorders, or injury. It is particularly hoped that such a more adaptive and flexible device would be useful in neurological disorders such as Parkinson's Disease. Other examples of neurological disorders potentially treatable with such a device include Multiple Sclerosis; epilepsy; pain; and more cognitive disorders such as Alzheimer's Disease, depression, bipolar disorder, Obsessive Compulsive Disorder, and addiction; and possibly even obesity. Moreover, the treatment may be used in rehabilitation therapy following stroke or traumatic brain injury.

Aspects of the invention will now be described by means of non-limiting example with reference to the following figures:

FIG. 9A shows an input signal.

FIG. 9B shows another input signal, delayed relative to the first input signal.

FIG. 9C shows a neurostimulator output.

FIG. 9D shows an alternative neurostimulator output.

The following additional patent documents are incorporated herein by reference: U.S. Pat. No. 5,913,882; WO2005053787A1; and US20050113744A1.

Figure 1A:
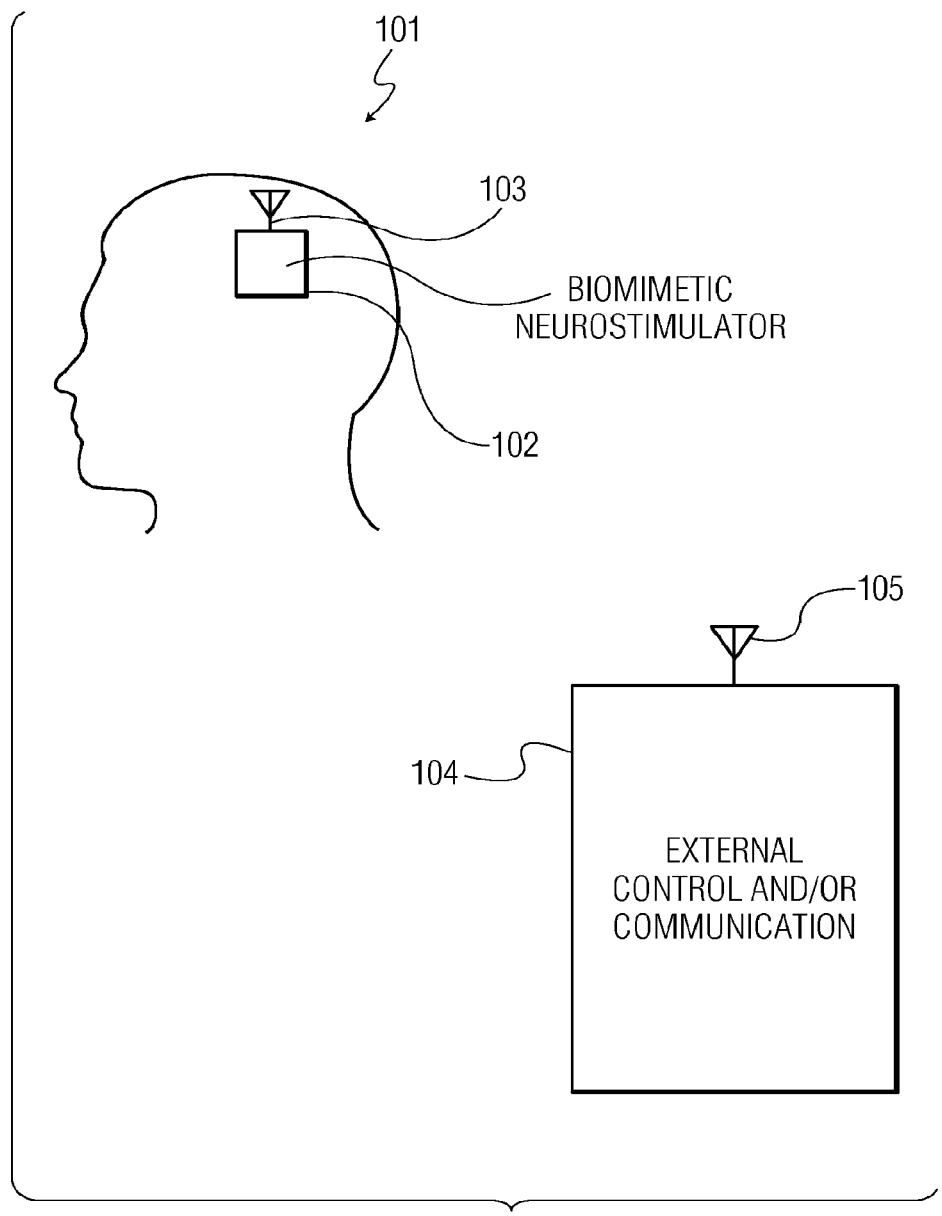
FIG. 1A is a schematic of a biomimetic neurostimulation device in a patient's head and an external control system.

FIG. 1A is a schematic of a patient's head 101 including a biomimetic neurostimulation device 102 provided with an optional antenna 103 (shown schematically) for external communication. Other types of external communication might be possible, such as a lead connected to the outside of the patient's skull. The device 102 is shown inside the brain, but it might be placed in other neural pathways, such as in the spinal column.

An optional external system 104 communicates with the device 102 via antenna 105. The external system 104 provides data to the device 102, for instance when a medical service provider detects progression of a disorder or from some sensor. The external system 104 may additionally or alternatively provide auxiliary processing or control for 102.

Figure 1B:
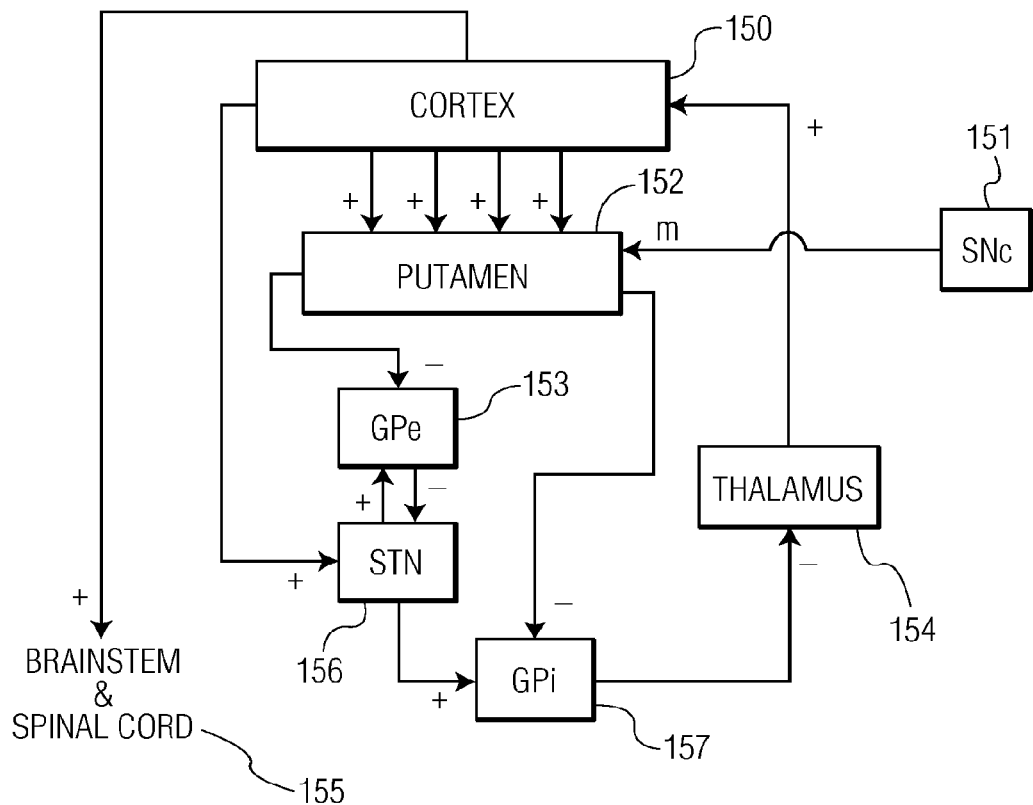
FIG. 1B is a schematized view of the circuit-like functioning of a portion of the brain.

As an example of typical brain circuits, FIG. 1B displays a schematic representation of the basal ganglia-thalamocortical motor circuits (Y. Temel et al., Progress in Neurobiology volume 76, pages 393-413 (2005)). This figure shows the cortex 150, substantia nigra pars compacta (SNc) 151, putamen 152, globus pallidus external segment (GPe) 153, thalamus 154, brain stem and spinal cord 155, subthalamic nucleus (STN) 156, and globus pallidus internal segment (GPi) 157. Excitatory connections are denoted by "+", inhibitory connections are denoted by "−", and modulatory connections are denoted by "m". The physiological functions schematized in this circuit are affected in motor diseases like Parkinson's disease, essential tremor, and dystonia for example. The proposed biomimetic neurostimulation device is well adapted to correct for pathological signals in such brain circuits.

Figure 2:
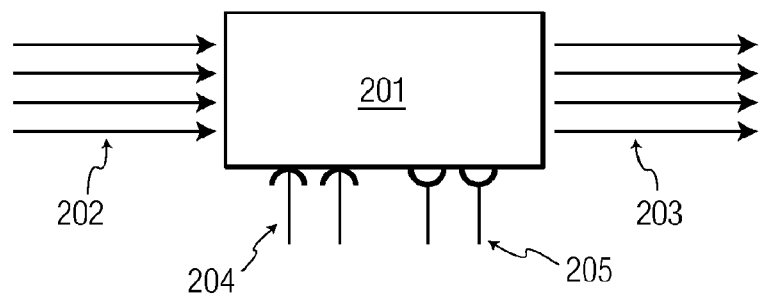
FIG. 2 is a more detailed schematic of part of FIG. 1B.

FIG. 2 is a more detailed schematic of a subpart of a brain circuit as displayed in FIG. 1B. The depicted region of the neurological system exhibits signal flow predominantly in a single direction. Some regions of motor control are particularly likely to have flow of this sort. In general, the flow will proceed from an afferent (upstream) region to an efferent (downstream) region. The circuit's sub-part receives afferent signals $\vec{I}$ at its (synaptic) inputs 202 and produces neurological signals $\vec{O}$ at its (synaptic) outputs 203. Four lines are shown as inputs 202 and as outputs 203. Four is an arbitrary number. In fact, signals from other regions of the brain or other neural pathway typically modulate the afferent signals in accordance with a very high dimensional input-output function $\vec{O}=F(\vec{I})$. In addition, the size of O and the size of I will generally differ. The modulating signals may be inhibitory 204 and/or excitatory 205 and in general comprise both feed-forward and feed-back signals. Both the afferent inputs and the modulatory signals are by nature non-stationary, so the output will be highly dynamic. Note that, as shown in FIG. 1B, bi-directional signal flow between regions (either direct or via larger circuits) is another general theme in neurological systems. The functioning of such circuits can be described in a similar way.

Figure 3:
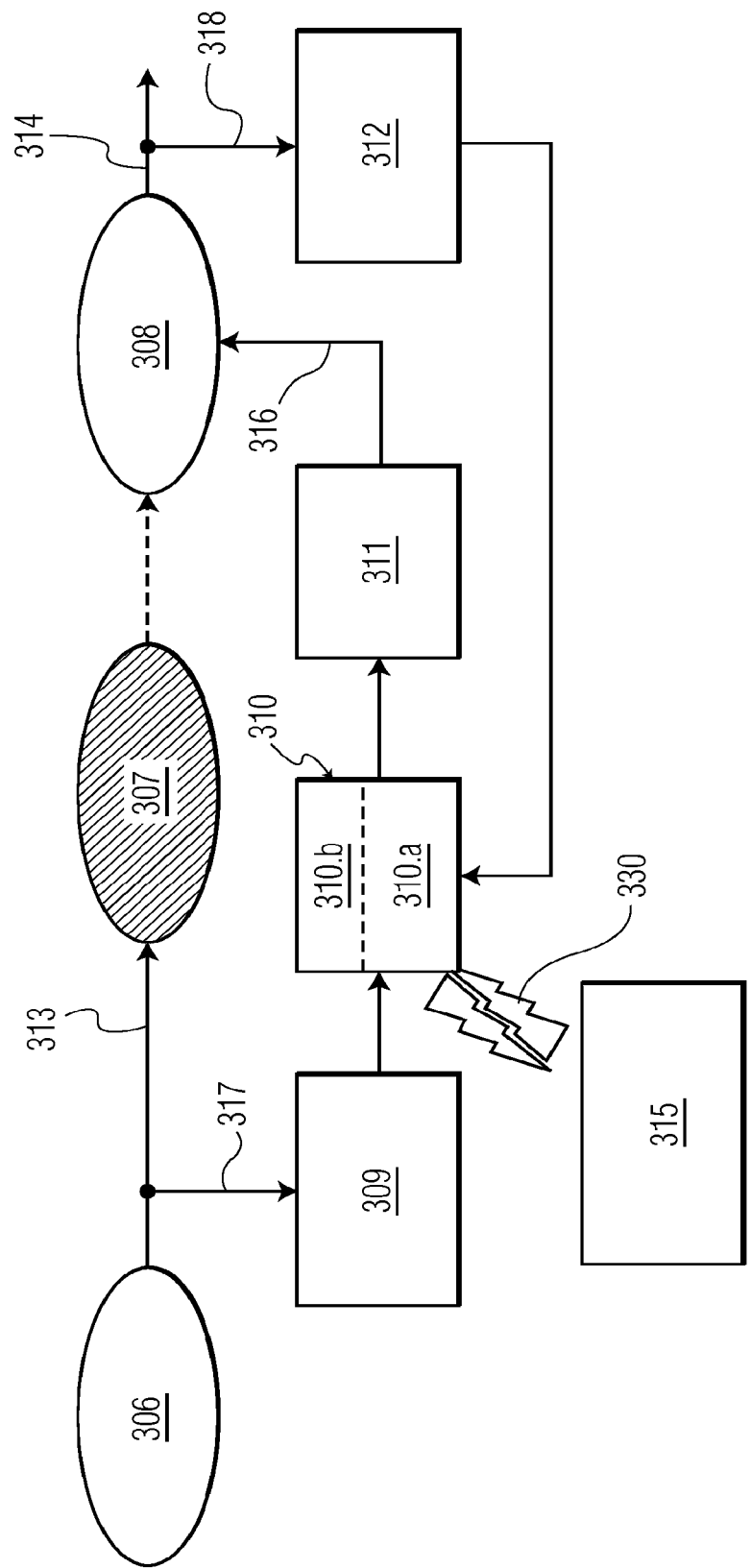
FIG. 3 shows a schematic of a biomimetic neurostimulator, implanted in a brain or nerve pathway.

FIG. 3 shows a schematic of a biomimetic neurostimulator, implanted in a brain or nerve pathway. The pathway includes three regions 306, 307, and 308. Regions 306 and 308 are expected to remain healthy, while region 307 is either compromised or expected to become compromised. Per FIG. 2, the primary flow of neural signals, is expected to be in one direction, e.g. from 306, to 307, to 308. The expected dysfunction of 307 is illustrated by illustrating signals 325 flowing out of it as a dotted line.

The implanted neurostimulator includes a first sensor 309; a processor 310 including a training/recording process 310a and a steady state process 310b; a stimulus emitter 311, and a second sensor 312. First sensor 309 takes an afferent signal 313 from the compromised region.

The stimulus emitter 311 is for example an electrical pulse generator. Stimulus emitter 311 provides a simulated response to region 308. Second sensor 312 takes an efferent signal 314 from region 308.

An optional external unit or units 315 communicate (wirelessly or otherwise) with the processor. External unit or units 315 may have a variety of optional features such as an additional sensor that senses some input other than neural activity (e.g., muscle activity, motion, digestion, or some other physiological or non-physiological parameter), or a supplemental processor, in case some function, especially training, requires more processor.

Element 316 is an output of the neuromimetic prosthetic device, while elements 317 and 318 are inputs.

Sensors 309 and 312 may be of many types including: electrical, optical, chemical, biochemical, electrochemical, magnetic or some combination of these. Stimulus emitter 311 may emit stimuli of many types including electrical, magnetic, optical, chemical, biochemical, or some combination of these. While only one sensor is drawn at 309 and at 312, more than one may be used. Similarly, while only one stimulus emitter 311 is drawn, more than one may be used. Moreover, more than one processor 310 with more than two subprocesses might be used as well.

Figure 4:
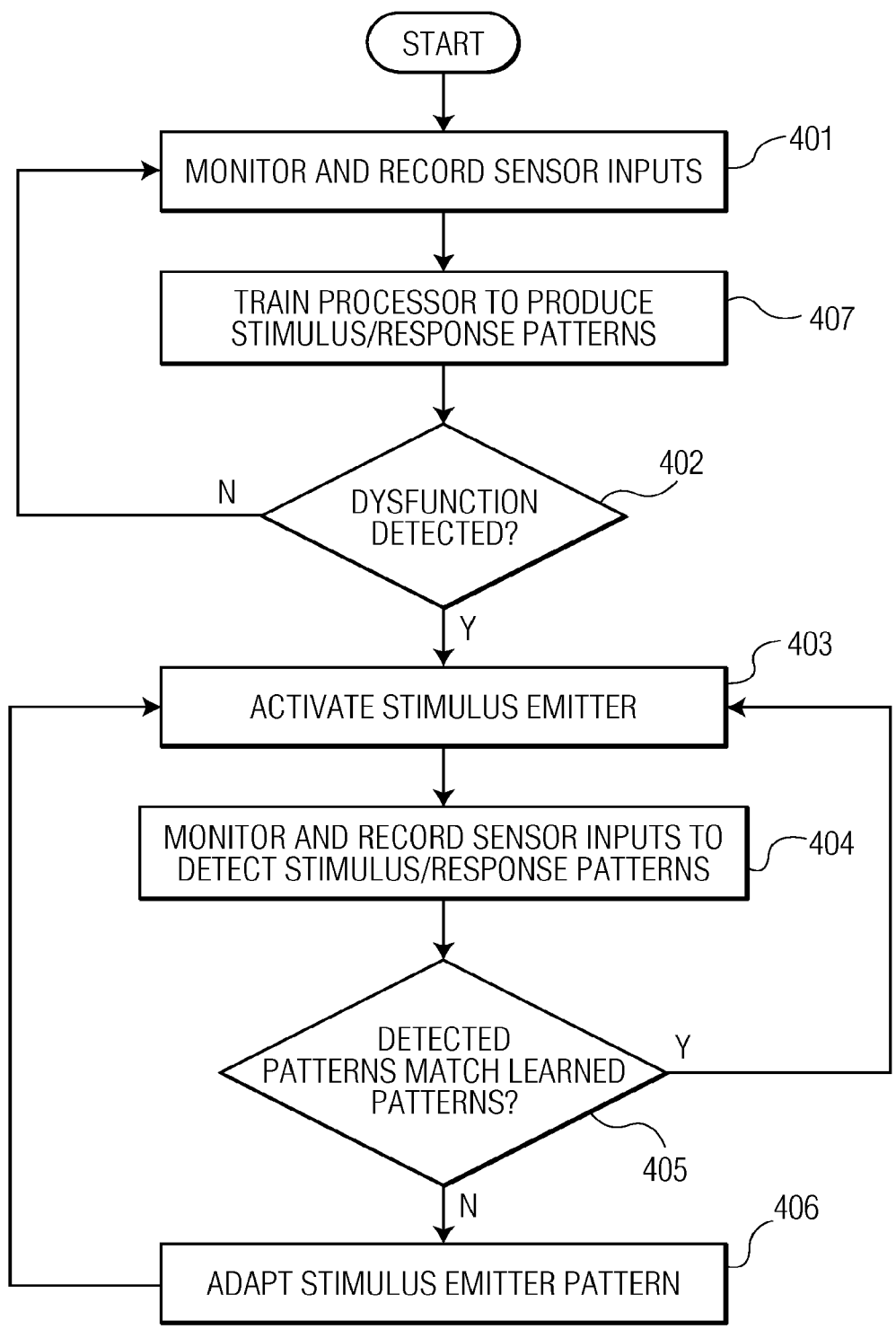
FIG. 4 is a flowchart showing stages of operation of the device of FIG. 3.

In another exemplary embodiment, processor 310 is designed to go through two stages of training, as shown in the flow chart of FIG. 4.

In the first stage, region 307 is presumed to be functioning at least to some degree. During the first stage, process 310a merely monitors signals 313 and 314 at step 401 and trains itself at step 407 in the stimulus/response pattern of response of regions 307 and 308 to signals at 313. Then processor 310 detects at step 402 that region 307 has become so compromised that its functioning must be replaced. Such detection may be in response to observations of changes in efferent signal 314. Alternatively, such detection may be in response to a signal 330 from an external unit 315, for instance if a doctor diagnoses sufficient deterioration as to require activation of the prosthetic device.

In the second stage of training, the process 310b continues to monitor signals 313 and 314; however, at step 403, it now activates stimulator emitter unit 311, directing it to provide some stimulation 316 to region 308. Then, at step 405, processor compares the signals 313 and 314 to see if they follow the stimulus/response patterns recorded during the first training stage. If observed patterns are different from the trained patterns, at step 406, the processor must adapt stimulus emitter patterns 316, return to step 403, monitor some more at step 404, and then at step 405 compare signals 313 and 314 again.

The second stage of training may continue indefinitely, continuing to adapt the emitted stimulus to the ongoing deterioration of region 307.

Alternatively, the prosthetic device uses only the second stage of training, with reference to a database of stimulus/response patterns. Such device is well suited for application following e.g. stroke or traumatic brain injury where an abrupt degradation of brain function has occurred as opposed to a gradual degradation due to progressive disease.

The training aspects of the process of FIG. 4 may be performed under control of an optional, external device 315. This is advantageous if the training process is computationally intensive and requires more hardware than would easily fit in an implanted device.

Optionally, the patient may be asked to perform tasks during the first and/or second stage of training.

Processor 310 incorporates a function that allows output that is transmitted to the stimulus emitter 311 (e.g., pulse-generator) to be derived from the sensed signals. This output may result, for instance, in amplitude or frequency or phase modulation of the electrical stimulus generated by the stimulus emitter 311. The function implemented in 310 can be complicated, such as described in the Berger paper. Alternatively, the processor may have simpler functions such as a relay function or a frequency transform function.

Means for sensing and analyzing detected neuronal signals are well known in the art. For instance, by using spike-detection algorithms (see e.g. Zumsteg et al., IEEE Transactions on Neural Systems and Rehabilitation Engineering, 2005, vol. 13, p 272-279) it is possible to determine the occurrence of neuronal spike signals detected by the sensing element(s). From this, a time sequence of action potentials can be obtained which can be further processed e.g. for frequency determination.

Figure 5:
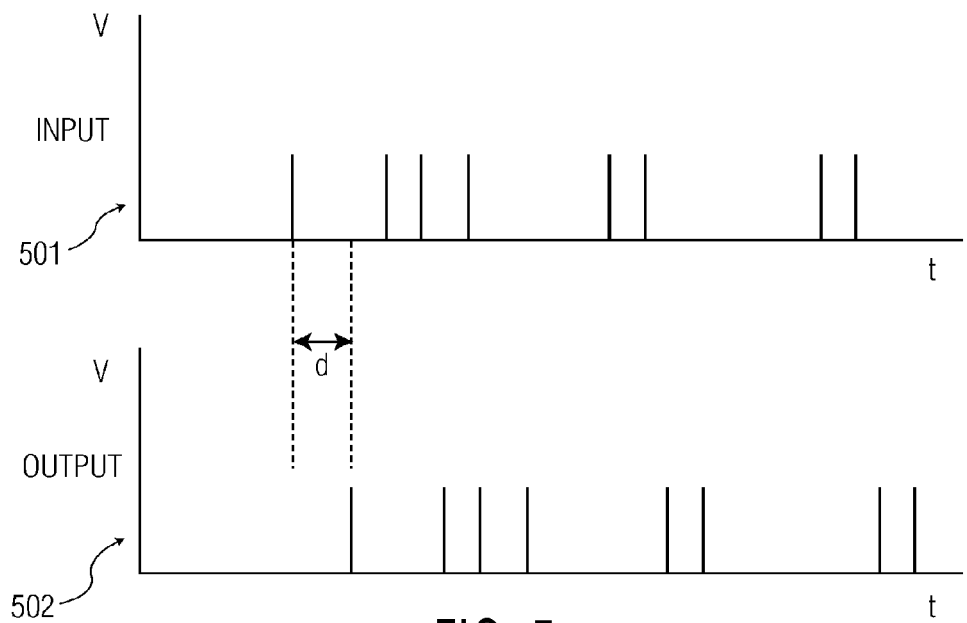
FIG. 5 illustrates a relay function.

FIG. 5 illustrates a relay function suitable for use by processor 310. This figure shows a sensed neural signal 501 and an output stimulus signal 502, having a fixed delay with respect to the sensed neural signal. After a neural signal has been detected (e.g. using above mentioned spike sorting methods) a stimulus pulse is generated after a given delay by the stimulator. Both signals are illustrated in terms of voltage as a function of time. A typical delay value d is 0.1-10 ms. The particular sequence of impulses is only an exemplary illustration. Other sequences may be used. Modulatory inputs may be used to increase/decrease this delay d.

Figure 6:
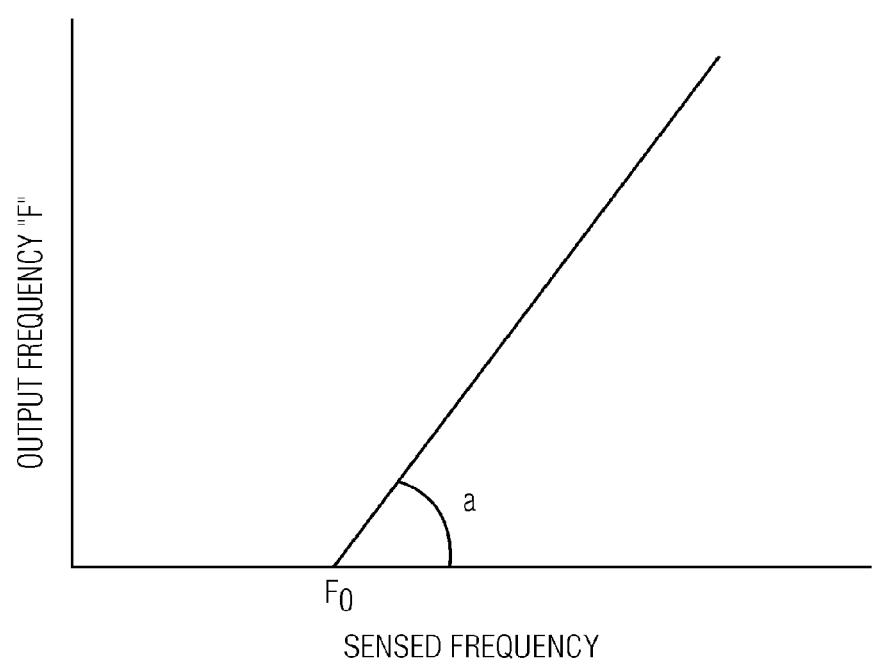
FIG. 6 illustrates a frequency transformation function.
Figure 7:
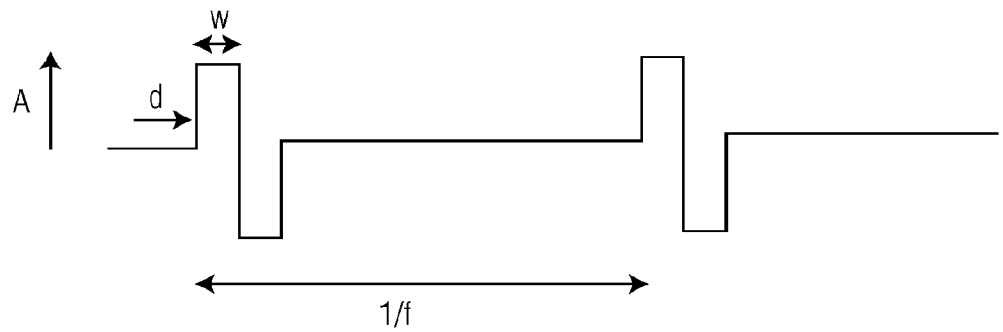
FIG. 7 illustrates a pulse train.

FIG. 6 illustrates a frequency transformation function alternatively suitable for use by processor 310. In this figure, the frequency of a sensed signal (action-potential-train, or field potential) shown on the horizontal axis is coupled to the frequency of the output pulse-train, shown on the vertical axis. In this figure F0 indicates the intercept with the horizontal axis and "a" indicates an angle with which the function intersects the horizontal axis. The "F0" and "a" can be modulated by other inputs, e.g. feedback signals, or other signals. The function is shown as linear here, but may take on other forms FIG. 7 illustrates a pulse train producible by stimulus emitter 311. The figure shows pulse voltage or current as a function of time. The figure shows a pulse of amplitude A, delay d', and width w. Typical ranges are amplitude of 0.1 to 4 volts (or 0.1-4 mA, depending on electrode impedance) and pulse width of 10-1000 µs.

It is particularly expected that dyskinesia, especially that associated with Parkinson's disease will respond to a prosthetic of the sort illustrated in FIG. 3, because dyskinesia is believed to be caused by excess stimulation, uncompensated by feedback, and not tuned to the exact intention by feedforward.

Figure 8:
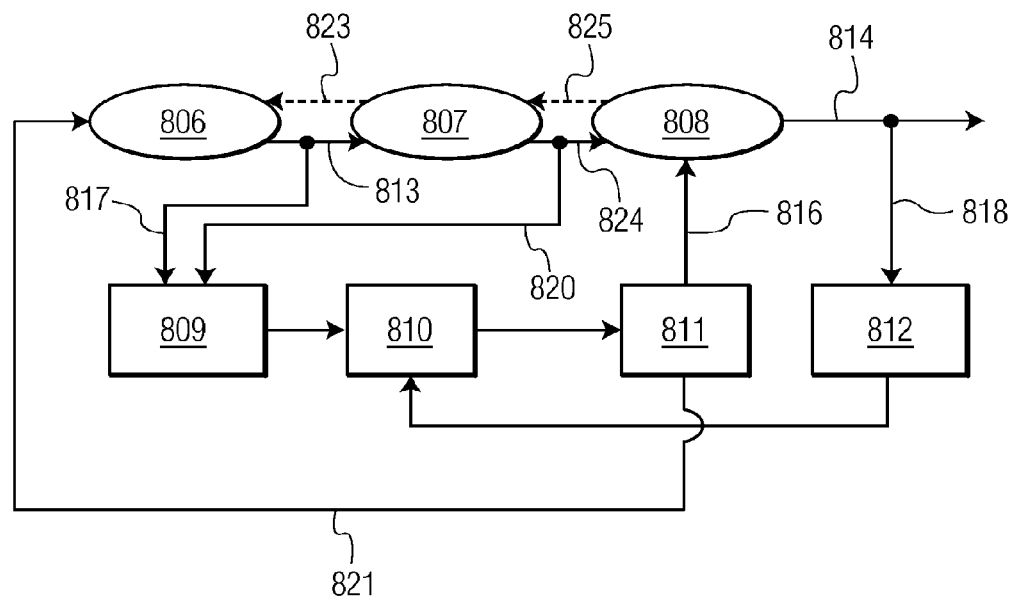
FIG. 8 shows an alternative embodiment to FIG. 3.

FIG. 8 shows an alternate embodiment to FIG. 3. In FIG. 8, the last two digits in the reference numerals of the boxes and ellipses indicate correspondence with those boxes and ellipses having the same last two digits in FIG. 3. In the embodiment of FIG. 8, the affected region 807 has bidirectional signal flow 813, 823, 824, 825 with the afferent and efferent regions. Outputs 823 and 825 from 807 are again illustrated with dotted lines indicating that they are expected to be compromised when region 807 becomes compromised. FIG. 8 includes two additional feedback pathways 820 and 821, not illustrated in FIG. 3.

FIGS. 9*a-d*. illustrate an embodiment of the modulation of neurostimulator output based on sensed signals. FIGS. 9A and 9B show two sensed signals, input 1 and input 2. Each sensed signal includes an input pulse 901 and 902, respectively. Here, an output characteristic is modulated according to sensed signals at two sensors. The modulation amplitude per time step is indicated by δ and in this example it is related to the time delay dt between detected signals on sensors 1 and 2. The output being modulated can be e.g. a continuous pulse train as indicated in FIG. 7 of which the modulation is applied to one or more parameters (e.g. pulse amplitude, pulse width, or pulse frequency). The value and sign of δ in this example depend on dt as indicated in the two sketches FIG. 9C and FIG. 9D. In the first case (FIG. 9C), for small positive dt, the modulation is strongly positive and drops for more positive dt values; for small negative dt the modulation is strongly negative, becoming less negative for more negative dt values. The second example (FIG. 9D) shows an alternative dependence of modulation on dt; it is close to zero for small dt values and has strongly positive (negative) value around a specific negative (positive) dt value and drops to zero again for large negative and positive dt values. Ultimately, the modulation the biomimetic prosthetic is trained to use will depend on what neurological function is to be replaced.

In general, the function performed by processors 310 and 810 will usually be learned by reference to experimental data and therefore not necessarily predictable in advance.

From reading the present disclosure, other modifications will be apparent to persons skilled in the art. Such modifications may involve other features which are already known in the design, manufacture and use of neurological prosthetic devices and which may be used instead of or in addition to features already described herein. Although claims have been formulated in this application to particular combinations of features, it should be understood that the scope of the disclosure of the present application also includes any novel feature or novel combination of features disclosed herein either explicitly or implicitly or any generalization thereof, whether or not it mitigates any or all of the same technical problems as does the present invention. The applicants hereby give notice that new claims may be formulated to such features during the prosecution of the present application or any further application derived therefrom.

The word "comprising", "comprise", or "comprises" as used herein should not be viewed as excluding additional elements. The singular article "a" or "an" as used herein should not be viewed as excluding a plurality of elements.

The invention claimed is:

1. A device comprising:
   at least first and second inputs configured to receive neural signals, the first input being disposed to receive signals afferent to a suspect neural region and the second input configured to receive signals from a neural region other than the suspect neural region;
   at least one output configured to emit neural compatible signals efferent to the suspect neural region; and
   at least one signal processing apparatus comprising a feed-forward path arranged between the first input and the output and a modulation path arranged to receive signals from the second input and provide a modulation signal to the feed-forward path.

2. The device of claim 1, wherein the neural region other than the suspect neural region is efferent to the suspect neural region.

3. The device of claim 1, wherein the feed-forward path comprises at least one processor for performing operations configured to:
   monitor signals received from the first and second inputs during a first time period;
   train the processor during the first time period to produce processing functions, the processing functions directing the emission of neural compatible signals via the output to produce signals received at the second input responsive to signals received at the first input;
   detect that the suspect neural region has become dysfunctional after the first time period;
   execute the produced processing functions during a second time period, the second time period after the first time period;
   monitor signals received from the first and second inputs during the second time period; and
   alter the processing functions during the second time period, responsive to a determination that signals received at the second input fail to match signals monitored during the first time period.

4. The device of claim 3, further comprising at least one third input for receiving signals generated externally to a patient's body and wherein the detecting is responsive to the signals received at the third input.

5. The device of claim 1, wherein the feedforward path comprises a stimulus emitter unit coupled to the output.

6. The device of claim 1, wherein the second input is arranged to receive signals efferent to the output, and wherein the modulation signal comprises feedback responsive to those efferent signals.

7. The device of claim 1, further comprising at least one third input for receiving signals generated externally to a patient's body.

8. The device of claim 1, wherein the feedforward path comprises:
   a first sensor arranged to receive first signals output from an afferent first neural region expected to remain healthy;
   a processor configured to learn and emulate functions of the suspect neural region, which is a second neural region; and
   a stimulus emitter arranged to supply signals to an efferent third neural region expected to remain healthy.

9. The device of claim 8, wherein the modulation path comprises a second sensor arranged to receive signals from a fourth neural region efferent to an output of the stimulus emitter and supply a modulation signal to the processor.

10. The device of claim 8, wherein:
    the suspect region communicates bidirectionally with the first and third neural regions;
    the first sensor is further arranged for receiving second signals efferent to the suspect neural region, but afferent to an output of the stimulus emitter unit; and
    the device further comprises a feedback path from the stimulus emitter unit to an area afferent to the first input to the first sensor.

11. The device of claim 8, wherein the suspect neural region is expected to communicate bidirectionally with adjacent tissue and the device further comprises:
    a first coupling to the first sensor from a region located between the suspect neural region and an output of the stimulus emitter unit; and
    a second coupling to the first neural region from the stimulus emitter unit.

12. A method for replacing suspect neural tissue the method comprising:
  implanting a device, the device comprising at least one output adapted to emit neural compatible signals efferent to a suspect neural region, at least first and second inputs configured to receive neural signals, the first input being disposed to receive neural signals afferent to the suspect neural region and the second input configured to receive neural signals efferent to the output, and at least one signal processing apparatus comprising a feedforward path coupling the first input and the output and a feedback path arranged to receive neural signals from the second input and to provide a feedback signal to the feedforward path;
  emitting at least one stimulus based on a processing function;
  monitoring signals received from the first and second inputs;
  comparing patterns of signals received at the first and second inputs; and
  adapting an emission pattern based on a result of the comparing.

13. The method of claim 12, further comprising:
  receiving signals received from the first and second inputs during a first time period;
  training the processing function during the first time period to produce signals received at the second input responsive to signals received at the first input;
  detecting that the suspect region has become dysfunctional after the first time period; and
  performing the emitting, monitoring, comparing, and adapting steps during a second time period, the second time period after the first time period.

14. The device of claim 3, wherein detecting that the suspect neural region has become dysfunctional after the first time period comprises:
  determining a first stimulus/response pattern during the first period of time based on signals received from the first and second inputs during the first time period; and
  detecting a change in the degree of function of the suspect neural region during the second time period based on a least one of:
    a difference in a second stimulus/response pattern and the first stimulus/response pattern, the second stimulus/response pattern comprising signals received from the first and second inputs during the second time period;
    a difference in the signal received at the second input during the second time period as compared to the signal received at the second input during the first time period; or
    an external signal received by the at least one processor for performing operations.

15. The device of claim 3, wherein training the processor during the first time period comprises:
  monitoring the first and second input in the absence of an emitted neural compatible signal;
  emitting neural compatible signals efferent to the suspect region via the at least one output according to a function;
  monitoring signals received at the second input in response to the emitted neural compatible signals; and
  comparing signals received at the second input in response to the emitted neural compatible signals to signals received at the second input in the absence of the emitted neural compatible signals.

16. The device of claim 15, wherein training the processor during the first time period further comprises:
  when the comparison of signals received at the second input in response to the emitted neural compatible signals to signals received at the second input in the absence of the emitted neural compatible signals indicates that the signals received at the second input in response to the emitted neural compatible signals approximate the signals received at the second input in the absence of the emitted neural compatible signals,
  recording the function producing the emitted neural compatible signal.

17. A method comprising:
  sensing an afferent neural signal afferent to a neural region of interest at a first time;
  sensing an efferent neural signal efferent to the neural region of interest at the first time;
  determining a first stimulus/response pattern based on the afferent neural signal and the efferent neural signal; and
  training a stimulator to maintain the function of the neural region of interest based on the determined first stimulus/response pattern.

18. The method of claim 17, further comprising:
  determining a degree of function of the neural region of interest at the first time;
  detecting a change in the degree of function of the neural region of interest at a second time based on a least one of:
    a difference in a second stimulus/response pattern and the first stimulus/response pattern, the second stimulus/response pattern based on the afferent neural signal and the efferent neural signal at the second time;
    a difference in the efferent neural signal at the second time as compared to the efferent neural signal at the first time; or
    an external signal from user input; and
  wherein training a stimulator to maintain the function of the neural region of interest comprises providing stimulus according to a stimulus emitter pattern, via a stimulator, to a second neural region efferent to the neural region of interest, the stimulus resulting in a third stimulus/response pattern matching the first stimulus/response pattern.

19. The method of claim 17, wherein the neural region of interest is a first region of interest, and wherein training the stimulator comprises:
  providing stimulus according to a stimulus emitter pattern to a second region of interest efferent to the first neural region of interest;
  sensing the efferent neural signal efferent to the first neural region of interest at a second time in response to the provided stimulus; and
  comparing the efferent neural signal efferent to the first neural region of interest at the second time to the efferent neural signal efferent to the first neural region of interest at the first time.

20. The method of claim 19, further comprising:
  in response to the efferent neural signal at the second time approximating the efferent neural signal at the first time, recording the stimulus emitter pattern in association with the first stimulus/response pattern.

21. The method of claim 17, wherein training the stimulator to maintain the function of the neural region of interest comprises recording the first stimulus/response pattern.

22. A system comprising:
  a first input configured to receive an afferent neural signal afferent to a neural region of interest at a first time;

a second input configured to receive an efferent neural signal efferent to the neural region of interest at the first time; and a processor configured to:
- determine a first stimulus/response pattern based on the afferent neural signal and the efferent neural signal at the first time; and
- train a stimulator to maintain the function of the neural region of interest based on the determined first stimulus/response pattern.

23. The system of claim 22, wherein the processor is further configured to:
- determine a degree of function of the neural region of interest at the first time based on the afferent neural signal and the efferent neural signal at the first time; and
- detect a change in the degree of function of the neural region of interest at a second time based on a least one of:
  - a difference in a second stimulus/response pattern and the first stimulus/response pattern, the second stimulus/response pattern based on the afferent neural signal and the efferent neural signal at a second time;
  - a difference in the efferent neural signal at the second time as compared to the efferent neural signal at the first time; or
  - user input via a user interface; and
- wherein the system further comprises the stimulator configured to provide stimulus according to a stimulus emitter pattern to a second neural region efferent to the neural region of interest, the stimulus resulting in a third stimulus/response pattern matching the first stimulus/response pattern.

24. The system of claim 22,
- wherein the neural region of interest is a first region of interest, the system further comprising the stimulator configured to provide stimulus according to a stimulus emitter pattern to a second region of interest efferent to the first region of interest;
- wherein the second input is configured to sense the efferent neural signal efferent to the first region of interest at a second time in response to the provided stimulus; and
- wherein the processor is further configured to compare the efferent neural signal efferent to the first neural region of interest at the second time to the efferent neural signal efferent to the first neural region of interest at the first time.

25. The system of claim 24, wherein the stimulator is configured to provide stimulus according to a stimulus emitter pattern recorded in association with the first stimulus/response pattern, in response to the processor determining that an afferent neural signal afferent to the first neural region of interest sensed via the first input at a third time is similar to the afferent neural signal afferent to the first neural region of interest at the first time.

26. The system of claim 25, wherein the second input is further configured to sense the efferent neural signal efferent to the first neural region of interest at a third time;
- wherein the processor if further configured to
  - determine a second stimulus/response pattern based on the afferent neural signal and the efferent neural signal at the third time; and
  - in response to determining the first stimulus/response pattern and the second stimulus response pattern do not match, adjusting the stimulus emitter pattern.

* * * * *